Figure 1:
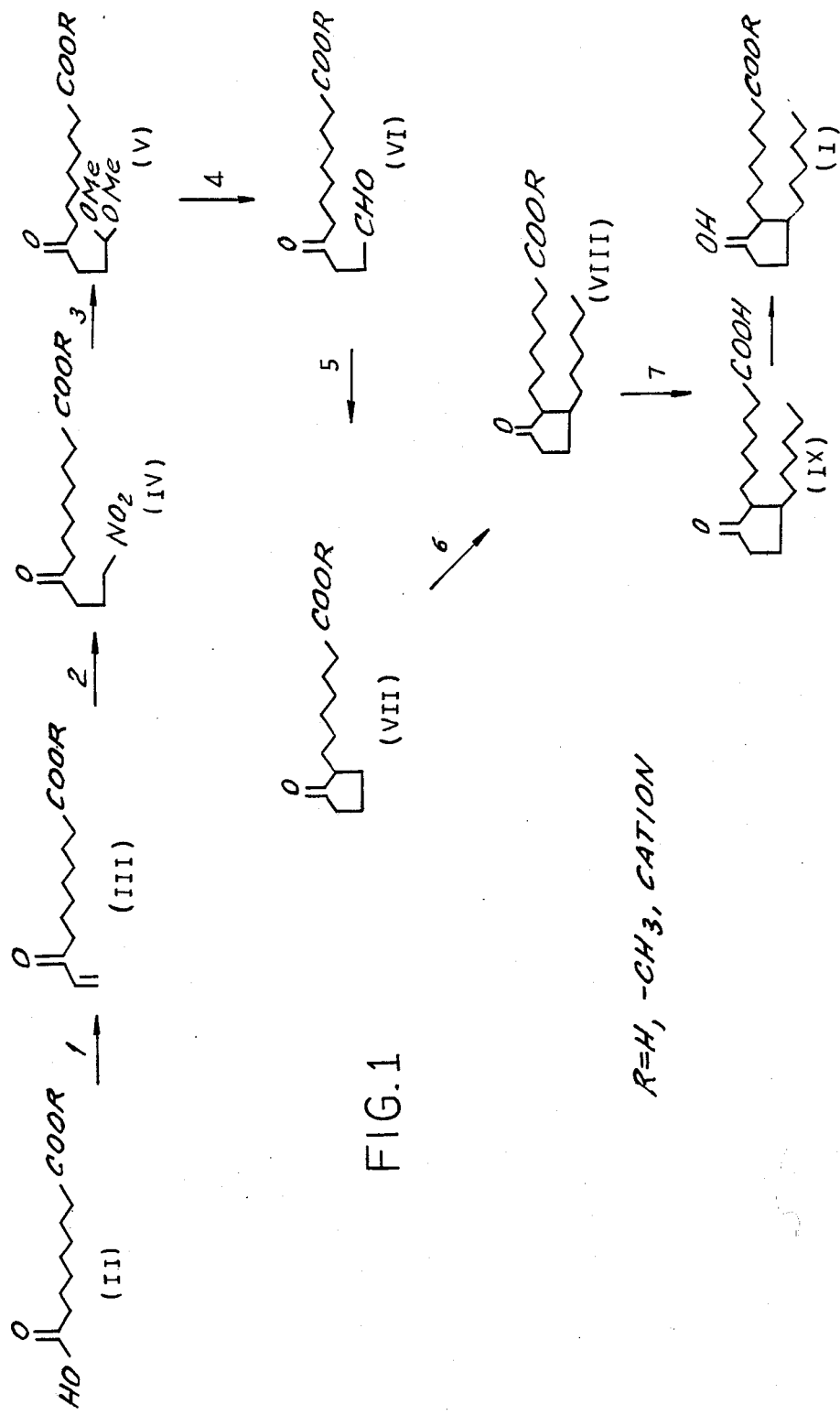

United States Patent [19]

Valcavi et al.

[11] Patent Number: 4,894,473
[45] Date of Patent: Jan. 16, 1990

[54] PROCESS FOR PREPARING 7-(2-HEXYL-5-HYDROXY-CYCLOPENTYL)-HEPTANOIC ACID

[75] Inventors: Umberto Valcavi, Milan; Sergio Innocenti, Melegnano; Enrico Bosone, Milan; Paolo Farina, Milan; Vittorio Marotta, Milan; Gianbattista Zabban, Milan, all of Italy

[73] Assignee: Istituto Biochimico Italiano Giovanni Lorenzini S.p.A., Italy

[21] Appl. No.: 117,669

[22] Filed: Nov. 5, 1987

Related U.S. Application Data

[63] Continuation of Ser. No. 744,406, Jun. 13, 1985, abandoned.

[30] Foreign Application Priority Data

Jan. 5, 1984 [IT] Italy .............................. 19043 A/84
Dec. 15, 1984 [EP] European Pat. Off. ............ 84115548
Jun. 27, 1985 [JP] Japan ........................... 60-139202

[51] Int. Cl.$^4$ ........................................ C07C 177/00
[52] U.S. Cl. .................................... 560/156; 560/121; 562/503; 562/567
[58] Field of Search ................ 560/121, 156; 562/503, 562/567

[56] References Cited

FOREIGN PATENT DOCUMENTS 155392 9/1985 European Pat. Off. ............ 560/121

Primary Examiner—Robert Gerstl
Attorney, Agent, or Firm—Ostrolenk, Faber, Gerb & Soffen

[57] ABSTRACT

A multistep process for preparing 7-(2-hexyl-5-hydroxy-cyclopentyl)-heptanoic acid is described. Novel intermediates are also described.

11 Claims, 1 Drawing Sheet

R=H, -CH₃, CATION

PROCESS FOR PREPARING 7-(2-HEXYL-5-HYDROXY-CYCLOPENTYL)-HEPTANOIC ACID

There is a continuation of Ser. No. 744,406, filed June 13, 1985 and now abandoned.

DESCRIPTION

The object of the present invention is to provide a new process for preparing 7-(2-hexyl-5-hydroxy-cyclopentyl)-heptanoic acid and the pharmacologically acceptable salts thereof, hereinafter identified as IBI-$C_{83}$.

Another object of the present invention is that of providing an improved process for the manufacture of IBI-$C_{83}$, particularly advantageous as: (a) it allows to use inexpensive raw materials which are easily found on the market; (b) it requires a smaller number of steps over the prior art processes; (c) the various process steps are simpler to be performed; (d) it enables to obtain higher end-product yields; (e) it is scarcely polluting and, therefore, affords a protection for the health of the workers and the environmental integrity; and finally, (f) it allows one to obtain a final product IBI-$C_{83}$ having high purity.

A further object of the present invention is that of providing new compounds useful as intermediates for the preparation of IBI-$C_{83}$.

These and other objects of the present invention will be more clearly seen from the description that follows.

7-(2-hexyl-5-hydroxy-cyclopentyl)-heptanoic acid and its pharmacologically acceptable salts are known for their anti-ulcer action (see for example: Arz. Forsch. 32 (I), 6, 657–663, 1982).

IBI-$C_{83}$ is described, inter alia, in the U.S.-A-4,073,938. In this patent, a process for the preparation of these compounds starting from ricinoleic acid is also described.

It has been found that, when operating by the improved process which is the subject of the present invention, it is possible to obtain a product having greater purity and a lower cost than the one obtained by the prior art.

Moreover, the process of the present invention requires raw materials which are less expensive and easily available and less polluting.

FIG. 1 shows some of the reactions according to the present invention useful for preparing the compound of formula (I) which foresee as the common intermediate, the methyl ester (VII) of 7-(5-keto-1-cyclopentenyl)-heptanoic acid.

When this intermediate has been obtained, alkylation at the position 1,4 is performed with alkyl-organocuprate, and ketone (VIII) is prepared. This latter is then converted to compound (I) according to per se known methods (v.e.g. U.S.-A-4,073,938).

Step (6) may be carried out by using organocuprates of the type R(PhS) CuLI, $R_2$CuLi, R(t-butoxy)CuLi, R(R'C≡C)CuLi, R(CN)CuLi (with R=n-hexyl) or also with Grignard reagents of the RMgX type in the presence of copper salts such as CuCl, Cu(OAc)$_2$, CuCN, CuI, CuCl$_2$, etc. Generally polar and inert solvents are used, such as THF, DMF, ethyl ether. Generally, the alkylation reactions at the position 1,4 are very critical, give low yields, are very expensive and cannot be performed on an industrial scale, since they involve the use of organocuprates containing lithium or the use of particular or expensive catalysts containing copper salts or copper salts in stoichiometric amount.

A method has now been found which can be applied on an industrial scale, which allows to obtain, with good yields, exclusively the trans isomer of compound (VIII) by adding at the position 1,4 hexyl magnesium bromide to sinton (VII) in the presence of catalytic amounts of CuJ, and by operating in tetrahydrofuran at temperatures between −70° C. and 10° C., in particular between −30° C. and −10° C.

This improved process is a further object of the present invention.

The first step (see FIG. 1) for the preparation of the common intermediate (VII) consists in a Fridel-Crafts reaction in ethylene and a subsequent dehydrohalogenation to obtain the vinylketone (III), which is converted into nitroketone (IV) by addition of nitromethane.

Afterwards, compound (IV) is converted into the ketoaldehyde (VI). This latter, by cyclization in a basic medium, enables to obtain, after esterification, the intermediate cyclopentenone (VII).

Step (1) consists in effect of three steps. In the first step the preparation of the chloride of the monomethylester of azelaic acid takes place by treatment with suitable chloridizing agents such as POCl$_3$, PCl$_5$, SOCl$_2$, etc., in suitable solvents.

The resulting chloride is then made to react with ethylene at a temperature between −10° C. and +60° C., in the presence of Lewis acids.

After having decomposed the organic salts by treating with water, dehydrohalogenation (3rd step) of the resulting β-chloroketone may be obtained with organic or inorganic bases in suitable solvents.

A particularly simple and advantageous method consists in performing the 1st step in methylene chloride, at reflux, using a slight excess of thionyl chloride. The resulting raw chloride is placed in methylene chloride in the presence of an excess of aluminum trichloride and into this suspension ethylene is bubbled at a temperature between 0° C. and 30° C.

After the end of the reaction and after washing with water, the resulting solution, containing the methyl ester of 12-chloro-9-keto-undecanoic acid, is refluxed with triethylamine.

If step (2) is carried out as generally described in literature, namely using nitromethane in the presence of inorganic or organic bases, this mainly leads to the formation (even when using a strong excess of nitromethane) of the bis-adduct reported below:

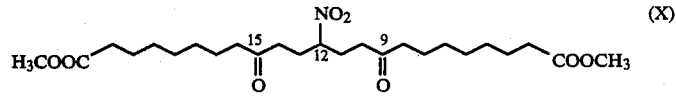

(G. P. Pollini, A. Barso, G. De Giuli; Synthesis 44, 1972, and refs. mentioned therein.—Yukaguku 31 (1), 35–8, 1982).

Due to this reason, after carefully investigating the process conditions, a method has been developed which allows to reduce to a maximum of 5% the formation of this bis-adduct.

This has been possible by pre-forming the nitronate anion by treating the excess nitromethane with equivalent amounts of organic or inorganic bases in lower alcohols or in mixtures of these alcohols with other organic solvents, such as e.g. methylene chloride, ethyl acetate, tetrahydrofuran, etc., and by subsequent dropwise addition of vinylketone (III) at a temperature of from −80° C. to 0° C.

According to a particularly preferred embodiment of the present invention, a solvent mixture is used consisting of methanol and methylene chloride or ethyl acetate in a ratio of between 1:1 and 5:1 (v/v); sodium methylate is used as a base, condensing at −20° C. for a period of 30 minutes to 5 hours.

Step (3) consists of two steps: at first nitroketone (IV) is treated with bases, such as e.g. NaOH, sodium methylate, potassium t-butylate, NaH, etc. in appropriate solvents, to obtain the corresponding nitronate anion. The suspension is then dripped into a mixture of methanol acidified with strong acids, such as e.g. hydrochloric hydrobromic, sulphuric acid etc. Preferably, sodium methylate in methanol can be used as a base, whereas sulphuric acid can be used as a strong acid.

The reaction of step (4) consists in the aqueous acidic hydrolysis of acetal (V). Inorganic acids may be used such as e.g. $H_2SO_4$, HBr, HCl, or organic acids such as e.g. HCOOH, $CH_3COOH$, p-tuolene sulphonic acid, $CF_3COOH$, etc. (or salts of these acids with organic bases) at various dilutions with water and using a suitable polar solvent such as e.g. tetrahydrofuran, dioxane, dimethylsulfoxide and acetone.

Preferably, 2N-hydrochloric acid and tetrahydrofuran at room temperature are used.

It has now been found that, more conveniently, steps (2), (3) and (4), rather than separately, may be performed in one single step using directly (in step 3) the nitronate anion of compound (IV) (present in suspension at the end of step (2), then treating succesively the raw acetal (V) with tetrahydrofuran and hydrochloric acid. The possibility of grouping into a single step the reaction of steps (2)-(4) was not known from the literature and, therefore, is a further object of the present invention. Actually, step (5) consists of two steps. In the first step aldehyde (VI) is treated in a basic medium. Since in this way a partial hydrolysis of the methyl ester (VII) occurs, the raw reaction product must be treated with suitable reagents for the re-esterification of the carboxyl. In particular, the first step is per se known in the literature [see for example: E. Wenkert: J. Am. Chem. Soc. 100, 1267 (1987)]. According to a preferred embodiment, it is particularly convenient to drip aldehyde (VI) into a refluxing solution of sodium methoxide in methanol.

For the second step, the known methods for preparing esters may be used. For example, good results are achieved by using methanol and concentrated hydrochloric acid.

Of this inventive process the following steps are particularly advantageous: step (2) [addition of nitromethane to the vinylketone (III)] and the improvement consisting in performing steps (2), (3) and (4) in one single step, which allows to considerably reduce both the consumption of material and the time of reduction, obtaining higher yields.

According to the instant invention, the methyl ester (VIII) can be transformed into the corresponding free acid by treating with potassium hydroxide in methanol and subsequent acidification with concentrated hydrochloric acid. The thus obtained free acid yields the 7-(2-hexyl-5-hydroxy-cyclopentyl)heptanoic acid of formula (I) either by chemical or microbiological reduction of the ketone group; the acid of formula (I) can in turn by reaction with a pharmacologically acceptable base yield the corresponding salt.

The following examples serve to better describe the preparation of various intermediates and of compound IBI-$C_{83}$ corresponding to formula (I) according to the process of the present invention.

The reaction conditions illustrated in the examples that follow do not limit the present invention but, as is known to the skilled artisan, may vary within relatively broad limits.

These reactions are carried out in glass multi-neck flasks provided (depending on the case) with thermometer, reflux cooler, reagent charging devices, Mivaris or 'Heavy Stirrer' magnetic stirrer.

The I.R. and N.M.R. analyses are carried out by means of a Perkin Elmer 157 G I.R. spectophotometer and an N.M.R. Varian 60 spectograph.

EXAMPLE 1

9-keto-10-undecenoic acid, methyl ester (III)

A solution of azelaic acid monomethyl ester (II) (21 g; 0.1 mole) and thionylchloride (15.4g; 0.13 mole) in methylene chloride (190 ml) is refluxed for 18 hours.

The thus obtained solution is added dropwise at 0° C. into a suspension of $AlCl_3$ (28.1 g; 0.21 mole) in methylene chloride (38 ml). After 10 minutes, ethylene (6 g; 0.21 mole) is bubbled into the solution for about 1 hour. It is poured into water/ice. the product is extracted with methylene chloride (3×20 ml). The organic extracts are washed with 5% $NaHCO_3$ solution (30 ml) and then with water (2×30 ml) and dried with $Na_2SO_4$. Triethylamine (16.6 g; 0.11 mole) is added to this solution, under stirring, and the mixture is refluxed for 2 hours. The mixture is poured into water and acidified with concentrated hydrochloric acid to pH 3.5, under stirring, and the phases are then separated. The organic phase is washed with water (30 ml) and dried to obain a yellow/orange oil, a sample of which is purified by silica gel chromatography (yield=100%).

I.R. (film): 1740, 1705, 1685, 1620 $cm^{-1}$ $^1$H-Nmr ($\delta$, $CDCl_3$): 1.0÷2.0 (m, 10H, $CH_2$) 2.2÷2.8 (m, 4H, $CH_2$—C=) 3.8 (s, 3H, $OCH_3$) 5.8÷6.2(m, 1H, =CH—C=O) 6.4÷6.6(m, 2H, $CH_2$=C)

U.V. (MeOH) $\lambda$ 215 nm E=8500

EXAMPLE 2

9-keto-12-nitro-dodecanoic acid, methyl ester (IV)

Nitromethane (12.8 g; 0.21 mole) is added dropwise to a solution of sodium methoxide, prepared from sodium (4.6 g; 0.2 mole) and methanol (200 ml), at 0°-5° C. The solution is cooled to −20° C. and 9-keto-10-undecanoic acid, methyl ester (III) (21.2 g; 0.1 mole) is added dropwise into the solution over 5 hours.

The mixture is stirred at −20° C. for 15 minutes and then poured into water/ice. By extraction with methylene chloride, a thick oil is obtained (20g). This is crystallized out of pentane (yield=73%).

($C_{13}H_{23}NO_5$ M.W.=273.3)

Analysis: m.p. 37°-8° C.

I.R.(nujol): 1735, 1715, 1560, 1380 $cm^{-1}$ $^1$H-NMR ($\delta$, $CDCl_3$): 1.2÷1.9 (m, 12H, $CH_2$) 2.1÷2.7 (m, 8H,

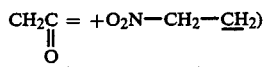

3.65 (s, 3H, OC$\underline{H}_3$) 4.4 (t, 2H, C$\underline{H}_2$—NO$_2$)

EXAMPLE 3

9-ketone-12-nitro-dodecanoic acid, methyl ester (IV)

Nitromethane (10.6 g) is added dropwise to a solution of sodium methoxide prepared from sodium (3.8 g; 0.2 mole) and methanol (165 ml) at 0°–5° C. Methylene chloride (165 ml) is added. the solution is cooled to −20° C. and then the methyl ester (III) (17.5 g) is added dropwise in 1 hour.

The mixture is stirred at −20° C. for 15 minutes and then poured into water/ice. The phases are separated, the aqueous layer extracted with methylene chloride to obtain a thick oil (16.5 g; yield=73%) that is crystallized with pentane to yield the ester (IV).

The analytical data corresponds to that of Example 2.

EXAMPLE 4

9-keto-12,12-dimethoxy-dodecanoic acid, methyl ester (V)

A solution of the acid (IV) (10 g; 0.037 mole), dissolved in methanol (30 ml) is added dropwise to a solution of sodium methoxide, prepared from sodium (0.85 g, 0.037 mole) and methanol (30 ml).

The thus obtained suspension is added dropwise, under stirring, at −35° C., to a mixture of 98% sulphuric acid (7 ml) and methanol (18.5 ml) in 20 minutes.

The temperature is allowed to reach −15° C. The mixture is poured into water/ice and extracted with methylene chloride (2×50 ml).

A reddish oil is obtained which after purification on silica gel yields the methyl ester (V) (8.1 g; 0.028 mole). (Yield=76%).

I.R. (nujol): 1735, 1715 cm$^{-1}$.

EXAMPLE 5

9-keto-12-nitro-dodecanoic acid, methyl ester (IV)

Nitromethane (10.6 g) is added dropwise to a solution at 0°–5° C. of sodium methoxide prepared from sodium (3.8 g; 0.2 mole) and methanol (165 ml). Ethylacetate (165 ml) is added. The solution is cooled to −20° C. and, in 1 hour, the methyl ester (III) (17.5 g) is added dropwise. The mixture is stirred at −20° C. for 15 minutes and then poured into water/ice. The phases are separated and extracted with ethyl acetate to obtain a thick oil (16.5 g; yield=73%) which is crystallized with pentane to yield the ester (IV).

The analytical data corresponds to that of Example 2.

EXAMPLE 6

9,12-diketo-dodecanoic acid, methyl ester (VI)

The methyl ester (V) (8.1 g, 0.028 mole) dissolved in tetrahydrofuran (14 ml) and 2N hydrochloric acid (7 ml) is stirred at room temperature for 1 hour.

A 30% sodium hydroxide solution (∼20 ml) is added up to a pH value of 6 and then the mixture is extracted with methylene chloride to obtain a dark oil which is purified by silica gel chromatography. The ester (VI) (6.5 g; yield=96%) is obtained.

I.R. (film): 2720—1730—1710 cm$^{-1}$ $^1$H-NMR (δ, CDCl$_3$): 1.05÷1.8 (m, 10H, CH$_2$) 2.3÷2.9 (m, 4H, CH$_2$—C$=$) 2.75 (s, 4H,

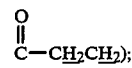

3.65 (s, 3H, OCH$_3$) 9.7 (s, 1H, C$\underline{H}$O) (C$_{13}$H$_{22}$O$_4$ M.W.=242.3)

|   | calculated | found |
|---|---|---|
| C | 64.43 | 64.22 |
| H | 9.15 | 9.32 |

EXAMPLE 7

9-keto-12-oxo-dodecanoic acid, methyl ester (VI)

Nitromethane (12.8 g; 0.21 mole) is added, dropwise, to a solution, at 0°–5° C., of sodium methoxide prepared from sodium (4.6 g; 0.2 mole) and methanol (200 ml). The mixture is cooled to −20° C. and the methyl ester of 9-keto-10-undecanoic acid (III) (21.2 g; 0.1 mole) is added dropwise in 5 hours. The mixture is stirred at −20° C. for 15 minutes. The thus obtained suspension is added dropwise at −35° C. into a mixture of 98% sulphuric acid (18.5 ml) and methanol (50 ml), in about 30 minutes.

The mixture is poured into water/ice and extracted with CH$_2$Cl$_2$ (4×100 ml).

The organic solution is washed with water (3×50 ml), dried and evaporated. The reddish residue is taken up with THF (100 ml) and 2N HCl (50 ml). The mixture is stirred at room temperature for 1 hour.

The mixture is treated with 30% NaOH solution (12 ml) until the pH value is adjusted to 6, the phases are separated, washed with water and salt. A dark red oil is obtained (23 g; yield=95%). A sample thereof is purified by means of silica gel chromatography.

The analytical data corresponds to that of Example 6.

EXAMPLE 8

7-(5-keto-cyclopentenyl)-heptanoic acid, methyl ester (VII)

A solution of the ester (VI) (10 g, 0.041 mole) in methanol (15 ml) is added dropwise, under nitrogen and stirring at reflux, to a solution of sodium methoxide [prepared from sodium (2.17 g; 0.094 mole) and methanol (280 ml)] At the end of the addition, the mixture is refluxed for 15 minutes.

The methanol is evaporated and the residue is treated with water/ice, acidified and extracted with methylene chloride (4×25 ml) and washed with water (3×25 ml).

After anhydration and evaporation, the residue is taken up with methanol (50 ml) and concentrated hydrochloric acid (1.5 ml). The mixture is stirred at room temperature for 18 hours.

The mixture is evaporated, taken up with methylene chloride (50 ml), washed with water (3×20 ml). A crude product is obtained (9 g) which is distilled in a bubble oven at about 0.7 mm/Hg (145°–148° C. (Yield=98%).

I.R. (liquid film): 1740, 1705, 1630, 1170 cm$^{-1}$.

$^1$H-NMR (δ, CDCl$_3$): 1.35÷2.4 (m, 16H, CH$_2$); 3.60 (s, 3H, OC$\underline{H}_3$) 7.26 (m, 1H, CH$=$).

EXAMPLE 9

7-(2-hexyl-5-keto-cyclopentyl)-heptanoic acid, methyl ester (VIII)

Hexylbromide (10 g; 0.06 mole) is added dropwise to a suspension of metallic magnesium (6.5 g, 0.27 mole) in tetrahydrofuran (188 ml) and a crystal of iodine is added. The mixture is heated to start the reaction and then the dropping of hexylbromide (36 g; 0.218 mole) is continued. At the end of the addition, the temperature is kept at 60° C. for 20 minutes until the magnesium is completely dissolved.

The mixture is cooled to 20° C. and diluted with tetrahydrofuran (188 ml). The mixture is cooled to 0°–5° C., and cuprous iodide (2.55 g; 0.0134 mole) is added. The mixture is stirred for 30–40 minutes until the solution becomes black.

The mixture is cooled to −20° C. and the methyl ester (VII) (30 g; 0.134 mole) is added dropwise, at the end of which a saturated ammonium chloride solution is added slowly. The phases are separated, the organic phase is washed to neutrality yielding a pale yellow oil (40.7 g; yield=98%).

I.R. (nujol): 1740 cm$^{-1}$ $^1$H-NMR ($\delta$, CDCl$_3$): 0.7÷1.8 (m, 26H, CH$_2$, CH$_3$+CH and CH cyclop.) 2.4 (m, 5H, CH$_2$—C=+-CH—C=) 3.65 (s, 3H, OCH$_3$)

C$_{19}$H$_{34}$O$_3$ M.W.=310.5)

|   | calculated | found |
|---|---|---|
| C | 73.50 | 73.46 |
| H | 11.04 | 11.07 |

EXAMPLE 10

7-(2-hexyl-5-keto-cyclopentyl)-heptanoic acid, methyl ester (VIII)

Hexylbromide (5.5 g) is added dropwise to a suspension of metallic magnesium (3.5 g) in ethyl ether (140 ml) and a crystal of iodine is added. The mixture is heated and then hexylbromide is added dropwise so as to keep the mixture at reflux.

At the end of the addition, the mixture is cooled to 5° C. and cupric acetate (2.8) is added. The mixture is stirred for 30 minutes. It is cooled to −40° C. and the methyl ester (VII) (16.2 g) is added dropwise in 20 minutes, at the end of which a solution saturated with ammonium chloride is added slowly.

The phases are separated, the organic phase is washed to neutrality yielding an oil (23.6 g) which, by purification by means of silica gel chromatography, yields the ester (VIII) (18.6 g; yield=83%).

The analytical data corresponds to that of Example 9.

EXAMPLE 11

7-(2-hexyl-5-keto-cyclopentyl)-heptanoic acid, methyl ester (VIII)

Hexylbromide (6.5 g) is added dropwise to a suspension of metallic magnesium (4.2 g) in tetrahydrofuran (120 ml) and a crystal of iodine is added. The mixture is heated to reflux and then the hexylbromide (23.3 g) is added dropwise. The mixture is kept for 20 minutes at 60° C. until the magnesium is completely dissolved. The solution is cooled to 20° C. and diluted with tetrahydrofuran (120 ml). The mixture is cooled to 0°–5° C. and cuprous chloride (2 g) is added.

The mixture is stirred for 30 minutes. It is cooled to −10° C. and the methyl ester (VII) (19.4 g) is added dropwise, at the end of which a saturated ammonium chloride solution (100 ml) is added slowly. The phases are separated, the organic phase is washed to neutrality to obtain an oil (27.8 g) which, purified by means of silica gel chromatography, yields the ester (VIII) (19.7 g; yield=73%).

The analytical data corresponds to that of Example 9.

EXAMPLE 12

7-(2-hexyl-5-keto-cyclopentyl)-heptanoic acid (IX)

A potassium hydroxide (15 g, 0.27 mole) solution in methanol (30 ml) is added with a solution of ester (VIII) (50 g, 0.16 mole) in methanol (120 g). The reaction mixture is refluxed for 2 hours. It is then cooled and concentrated under reduced pressure, poured into water (200 ml) and acidified with conc. hydrochloric acid. It is then extracted with ethyl acetate (3×100 ml). The acid (IX) (13 g) is obtained. Yield=27%.

I.R. (nujol): 3400, 3000, 1740, 1700 cm$^{-1}$ $^1$H NMR ($\delta$: CDCl$_3$): 0.9 (t, 3H, CH$_3$); 1.1÷1.8 (m, 23H aliph. CH$_2$ and CH) 2.0÷2.4(m, 5H, CH$_2$—C= and CH—C=) 9.6 (s, 1H, COO$\underline{H}$)

EXAMPLE 13

7-(2-hexyl-5-hydroxy-cyclopentyl)-heptanoic acid (I)

7-(2-hexyl-5-keto-cyclopentyl)-heptanoic acid (IX) 38 g; 0.128 mole) is dissolved at room temperature in a solution of sodium hydroxide (6.16 g; 0.154 mole) in methanol (190 ml).

After cooling to 0° C., sodium borohydride (2.44 g; 0.064 mole) is added portionwise in 20 minutes. The mixture is stirred at room temperature overnight, evaporated and the residue taken up with water (380 ml).

The mixture is acidified to ph4 with 6N hydrochloric acid and stirred for 1 hour. The precipitate is filtered off to obtain 7-(2-hexyl-5-hydroxy-cyclopentyl)-heptanoic acid (I) (33.8 g; yield=88.5%).

I.R. (nujol) 3460, 1725, 1460, 1390 cm$^{-1}$ $^1$H-NMR ($\delta$, CDCl$_3$): 0.9 (t, 3H, CH$_2$CH$_3$); 1.15÷1.8 (m, 26H, CH$_2$); 2.3 (t, 2H, CH$_2$—COO$\underline{H}$); 3.9 (m, ¾H, CH—OH) 4.20 (t, ¼H, C$\underline{H}$—$\overline{O}$H); 7.1 (m, 2H, COOH-+OH)

(C$_{18}$H$_{34}$O$_3$ M.W.=298.5)

|   | calculated | found |
|---|---|---|
| C | 72.43 | 72.26 |
| H | 11.48 | 11.66 |

EXAMPLE 14

7-(2-hexyl-5-hydroxy-cyclopentyl)-heptanoic acid (I)

The cells of yeast (*Saccaromyces cerevisiae*-160 g) are suspended in 1 liter of medium containing D glucose (180 g), KHPO$_4$ (0.38 g) and MgSO$_4$ (0.19 g).

7-(2-hexyl-5-keto-cyclopentyl)-heptanoic acid (IX) (1.48 g) dissolved in ethanol (15 ml) and water (25 ml) is filtered off, in sterile conditions, by means of a Millipore FHLP 01300 membrane and it is added to the suspension distributed in 500 ml Erlenmeyer flasks (50 ml per flask).

The mixture is stirred at 30° C. by rotative shaker at 200 r.p.m. for 48 hours; the suspensions are collected, ethylacetate (300 ml) is added and the mixture is filtered on Celite. The organic layer is evaporated under reduced pressure. The residue (6 g) is purified by silica-column chromatography. Acid (I) is obtained (1.28 g; yield=86%).

The analytical data corresponds to that of the product of Example 13.

We claim:

1. A compound having the formula

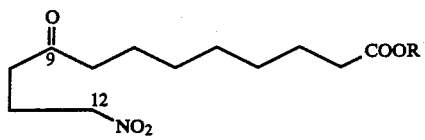

wherein R=H, CH₃, C₂H₅, C₃H₇ or C₄H₉.

2. A process for preparing 7-(2-hexyl-5-hydroxy-cyclopentyl)-heptanoic acid comprising the sequential steps of (a) reacting the chlorinated monomethyl ester of azelaic acid with ethylene in the presence of a Lewis acid at a temperature of −10° to 60° C. so as to form the methyl ester of 12-chloro-9-keto-undecanoic acid, (b) dehydrohalogenating the methyl ester of 12-chloro-9-keto-undecanoic acid by refluxing the ester in the presence of a base, (c) contacting the resulting reaction mixture containing the methyl ester of 9-keto-10-undecanoic acid with nitromethane and a base in an alcoholic solvent at a temperature of −80° to 0° C. so as to form the methyl ester of 9-keto-12-nitrodecanoic acid, (d) converting the 12-nitro group in the methyl ester of 9-keto-12-nitro-decanoic acid to a 12-dimethoxy group by contact with methanol, (e) hydrolyzing the 12-dimethoxy compound to the methyl ester of 9-keto-12-oxy-decanoic acid, (f) converting the methyl ester of 9-keto-12-oxo-decanoic acid into 7-(5-keto-cyclopentenyl)-heptanoic acid, (g) reacting the resulting heptanoic acid with an esterifying agent and then with hexylmagnesium bromide in the presence of a catalytic amount of a cuprous salt at a temperature of −70° to 10° C. so as to form an ester of 7-(2-hexyl-5-keto-cyclopentyl)-heptanoic acid, (h) hydrolyzing the ester to 7-(2-hexyl-5-keto-cyclopentyl)-heptanoic acid and (i) reducing the ketone group of said acid so as to produce 7-(2-hexyl-5-hydroxy-cyclopentyl)-heptanoic acid.

3. The process of claim 2 in which step (c) is effected by combining the methyl ester of 9-keto-10-undecanoic acid with a solution of nitromethane in methanolic sodium hydroxide or sodium methoxide at a temperature from −50° to −10° C. for a time ranging from 30 minutes to 5 hours.

4. The process of claim 3 wherein the hydrolysis step (e) is effected with hydrochloric acid.

5. The process of claim 3 wherein the converting step (d) comprises contacting the methyl ester of 9-keto-12-nitrodecanoic acid with a base and then with a methanolic acid at a temperature from −30° to −50° C.

6. The method of claim 2 further comprising the step of chlorinating the methyl ester of azelaic acid so as to form the chlorinated reactant of step (a).

7. The process of claim 6 in which the chlorinating agent is thionyl chloride.

8. The process of claim 2 in which the Lewis acid of step (a) is aluminum chloride and the temperature is 0° to 30° C.

9. The process of claim 2 in which the cuprous salt is cuprous iodide.

10. The process of claim 2 in which the 7-(2-hexyl-5-hydroxy-cyclopentyl)-heptanoic acid is further reacted with a pharmaceutically acceptable base so as to form a salt thereof.

11. A process for preparing 7-(2-hexyl-5-hydroxy-cyclopentyl)-heptanoic acid comprising the sequential steps of (a) reacting the chlorinated monomethyl ester of azelaic acid with ethylene in the presence of a Lewis acid at a temperature of −10° to 60° C. so as to form the methyl ester of 12-chloro-9-keto-undecanoic acid, (b) dehydrohalogenating the methyl ester of 12-chloro-9-keto-undecanoic acid by refluxing the ester in the presence of a base, (c) contacting the resulting reaction mixture containing the methyl ester of 9-keto-10-undecanoic acid with nitromethane and a base in an alcoholic solvent at a temperature of −80° to 0° C. so as to form the methyl ester of 9-keto-12-nitrodecanoic acid, (d) combining the resulting reaction mixture with tetrahydrofuran and hydrochloric acid so as to form the methyl ester of 9-keto-12-oxodecanoic acid (e) converting the methyl ester of 9-keto-12-oxo-decanoic acid into 7-(5-keto-cyclopentenyl)-heptanoic acid, (f) reacting the resulting heptanoic acid with an esterifying agent and then with hexylmagnesium bromide in the presence of a catalytic amount of a cuprous salt at a temperature of −70° to 10° C. so as to form an ester of 7-(2-hexyl-5-keto-cyclopentyl)-heptanoic acid, (g) hydrolyzing the ester to 7-(2-hexyl-5-keto-cyclopentyl)-heptanoic acid and (h) reducing the ketone group of said acid so as to produce 7-(2-hexyl-5-hydroxy-cyclopentyl)-heptanoic acid.

* * * * *